United States Patent

Von Baeyer et al.

[11] Patent Number: 6,060,232
[45] Date of Patent: May 9, 2000

[54] ORGAN STORAGE SOLUTION

[75] Inventors: Hans Von Baeyer, Berlin; Bernd Steinbach, Friedberg; Hans-Jurgen Flaig, Lauterbach, all of Germany

[73] Assignee: Fresenius Medical Care Deutschland GmbH, Bad Homburg, Germany

[21] Appl. No.: 09/024,589

[22] Filed: Feb. 17, 1998

[30] Foreign Application Priority Data

Feb. 17, 1997 [DE] Germany .............. 197 06 111

[51] Int. Cl.$^7$ ...................................... A01N 1/02
[52] U.S. Cl. .............. 435/1.1; 435/1.1; 435/1.2; 435/1.3; 435/2
[58] Field of Search ............. 435/1.1, 1.2, 1.3, 435/2

[56] References Cited

U.S. PATENT DOCUMENTS

| | | | |
|---|---|---|---|
| 4,879,283 | 11/1989 | Belzer et al. | 514/60 |
| 4,938,961 | 7/1990 | Collins et al. | 424/606 |
| 5,370,989 | 12/1994 | Stern et al. | |
| 5,498,519 | 3/1996 | Rubin et al. | |

FOREIGN PATENT DOCUMENTS

| | | |
|---|---|---|
| 526 331 | 11/1976 | U.S.S.R. |
| 545 312 | 2/1977 | U.S.S.R. |
| 971 190 | 11/1982 | U.S.S.R. |
| 1 109 110 | 8/1984 | U.S.S.R. |
| 95/02326 | 1/1995 | WIPO |

OTHER PUBLICATIONS

Marsh et al., "Hypothermic preservation of hepatocytes. I. Role of cell swelling", Cryobiology 26 (6) : 524–34 (1989).

Abaas, "Induction of aggregation in *Streptococcus–mitis* by cerain ions", Acta Pathol. Micorbiol. Immunol. Scand. Sect. B Microbiol. 92 (5) : 253–260 (1984).

Nakae S., "Preservation of the Normothermic, Anoxic Canine Heart, Lung, Kidney with Metabolic Inhibitor", Kyorin Igakki Zasshi 9(4):235–40 (1978) Abstract Only.

*Primary Examiner*—Sandra E. Saucier
*Attorney, Agent, or Firm*—Kenyon & Kenyon

[57] ABSTRACT

The invention relates to a solution for storing organs, preferably kidneys. To effectively prevent organ damage, the solution has a high sulfate content and a low chloride content. In particular, the solution comprises about $Na^+$(2–30 mM), $K^+$(70–130 mM), MgH(30–40 mM), $Ce^-$(2–20 mM), $SO_4^{2-}$(80–95 mM) and raffinose (20–60 mM) at aph of about 7.4.

7 Claims, No Drawings

ORGAN STORAGE SOLUTION

BACKGROUND AND FIELD OF THE INVENTION

The invention relates to an organ storage solution, which is suitable for organ preservation.

In the explantation of organs from a host body, for example, a kidney, heart, liver, or pancreas, ischemic organic damage occurs regularly and cannot be controlled as yet. The extent of damage depends on the so-called "warm ischemia time." This time is defined as the period between the clamping off of the supplying artery and the start of cooling of the isolated organs, whether by cold storage alone or by cold storage in combination with perfusion with a preservation solution. The so-called UW solution or the Euro-Collins solution, for example, is already being used as a preservation solution.

A cause of the ischemic damage is the continuation of energy-utilizing metabolic reactions in the suddenly ischemic tissue. After aerobic glycolysis ceases, anaerobic glycolysis occurs as the energy-supplying reaction. As a result, tissue-damaging metabolites, such as lactic acid, form, which because of their acidic nature lower cell pH. If circulation is available, the metabolites are carried away and detoxified in the liver (Cori cycle).

Avoidance of ischemic damage is essential for the immediate resumption of organ function after explantation in the recipient's body or in the perfusion apparatus.

Another field of application of organ preservation is the use of slaughterhouse organs as substitutes for animal experiments. To perform such studies on slaughterhouse organs, the organ must be preserved immediately after slaughter. These organs in which the studies are to be performed must be kept as long as possible in a physiological environment with unaltered metabolic properties.

DESCRIPTION OF THE PREFERRED EMBODIMENTS

An object of the invention is to provide a solution for the storage of organs, i.e., a so-called organoplegic solution, which makes it possible to keep organs as long as possible in a physiological environment with unaltered metabolic properties.

According to the invention, this object can be attained by a solution having a high sulfate content, preferably at least 80 mM, and a low chloride content, preferably less than 20 mM. A solution with a high sulfate, magnesium, and potassium content and a low chloride and sodium content is preferred. The intention is to block energy-dependent, transmembrane ion transport with the solution, so that the pressure for energy consumption in the ischemic tissue is eliminated. This can be achieved by transport blockade of the following ion channels:

| Ion species | Blockade |
| --- | --- |
| Magnesium | Calcium channels |
| Sulfate | Anion channels |
| Potassium | Sodium channels |

The transport blockade of the cited ion channels can inhibit oxygen consumption caused by transmembrane ion transport. The damage caused by anaerobic oxygen consumption in ischemic tissue, as was described above, is therefore decreased by the suitable novel solutions according to the invention.

An especially advantageous embodiment of the invention results from a composition of the solution which contains at least the following components per 1000 mL of solution at a pH of approximately 7.40:

| Species | Concentration Range | Osmolarity Range |
| --- | --- | --- |
| $Na^+$ | approx. 2–30 mmol/L | 2–30 mOsm |
| $K^+$ | approx. 70–130 mmol/L | 70–130 mOsm |
| $Mg^{++}$ | approx. 30–40 mmol/L | 60–80 mOsm |
| $Cl^-$ | approx. 2–20 mmol/L | 2–20 mOsm |
| $SO_4^{2-}$ | approx. 80–95 mmol/L | 60–70 mOsm |
| Raffinose | approx. 20–60 mmol/L | 30–60 mOsm |

Sodium transport is inhibited in addition here by the relatively high potassium concentration. Thus, another mechanism exists which increases the effectiveness of the solution still further.

Preferably, the sulfate content of the solution of the invention is at least 80 mM, and the chloride content is less than 20 mM. The solution also can contain a polyethylene glycol component. If present, a polyethylene glycol having a molecular weight of about 4600 is preferred. Most preferably, the polyethylene glycol content of the solution is 10 percent by weight, when employed. The pH of the solutions of the invention can be controlled by a buffer, preferably a phosphate buffer.

A particularly preferred solution of the invention contains the following components per 1000 ml of solution at a pH of approximately 7.4:

| Species | Concentration | Osmolarity |
| --- | --- | --- |
| $Na^+$ | 10 mmol/L | 10 mOsm |
| $K^+$ | 100 mmol/L | 100 mOsm |
| $Mg^{++}$ | 35 mmol/L | 70 mOsm |
| $Cl^-$ | 10 mmol/L | 10 mOsm |
| $SO_4^{2-}$ | 85 mmol/L | 65 mOsm |
| Raffinose | 50 mmol/L | 50 mOsm |

A particularly preferred solution of the invention consists essentially of 10 mM NaCl (20 mOsm), 35 mM $MgSO_4$ (70 mOsm), 50 mM $K_2SO_4$ (150 mOsm), 50 mM raffinose (50 mOsm), and 10% polyethylene glycol in a phosphate buffer (3 mM), having a pH of 7.4, and having a total osmolarity of approximately 290 mOsm.

The solutions of the invention can be administered, for example, according to the following two approaches during use according to regional legal slaughtering provisions for the preservation of slaughterhouse organs:

1. The solution can be introduced into a donor's body by means of a blood vessel catheter. No special anesthesia is necessary with individuals in whom brain death has been established. In slaughterhouse animals typical stunning, e.g., with electric shock, is necessary.

Vascular access can be created by puncturing the femoral artery. A vascular catheter, which can be a single-lumen Shaldon dialysis catheter, is advanced to the level of the abdominal aorta in the region of the origin of the renal arteries. After this region is reached, which is evident from the pressure amplitude typical for the abdominal aorta and measurable with a connected pressure sensor, an "organoplegic solution" according to the invention is infused at a flow rate of 300 mL/min, e.g., by means of a roller pump. At the same time, the donor animal is rapidly exsanguinated by unilateral incision of cervical vessels with severance of the carotid artery and the jugular vein. The infusion process is continued until complete exsanguination. This is evident from cardiac arrest, which is also produced by the infusion.

2. If an infusion of the slaughtered animal is not permitted, the arterial supply of the organ to be removed is immediately cannulated after opening of the abdominal cavity by means of a median incision and the infusion is begun by means of a pump. The organ is then removed by severing the other vessels (in the case of the kidney, veins and ureter).

The organs are perfused with the organoplegic solution until the venous outflow is macroscopically free of blood.

The organ is then stored in a plastic container on ice.

After connection, perfusion with perfusion blood is continued until the venous outflow again resembles blood. The organ can then be brought into the closed perfusion circulation.

The use of the solution according to the invention enables the removal of slaughterhouse organs for organ perfusion as an animal substitute method. Further, it also improves the results of organ transplantation, particularly kidney transplantation, in human medicine.

What is claimed is:

1. A solution for the storage of organs, coonsisting essentially of the following components per 1000 mL of solution, at a pH of approximately 7.4:

| Species | Concentration Range |
| --- | --- |
| $Na^+$ | about 2–30 mmol/L |
| $K^+$ | about 70–130 mmol/L |
| $Mg^{++}$ | about 30–40 mmol/L |
| $Cl^-$ | about 2–20 mmol/L |
| $SO_4^{2-}$ | about 80–95 mmol/L |
| Raffinose | about 20–60 mmol/L |

2. The solution of claim 1, consisting essentially of the following components per 1000 mL of solution, at a pH of approximately 7.4:

| Species | Concentration |
| --- | --- |
| $Na^+$ | 10 mmol/L |
| $K^+$ | 100 mmol/L |
| $Mg^{++}$ | 35 mmol/L |
| $Cl^-$ | 10 mmol/L |
| $SO_4^{3-}$ | 85 mmol/L |
| Raffinose | 50 mmol/L |

3. The solution of claim 2, wherein the pH is adjusted with a phosphate buffer.

4. A solution for the storage of organs, consisting essentially of 10 mM NaCl, 35 mM $MgSO_4$, 50 mM $K_2SO_4$, 50 mM raffinose, and 10% polyethylene glycol in a phosphate buffer (3 mM), having a pH of 7.4.

5. A solution for the storage of organs, consisting essentially of a polyethylene glycol and the following components per 1000 mL of solution, at a pH of approximately 7.4:

| Species | Concentration Range |
| --- | --- |
| $Na^+$ | about 2–30 mmol/L |
| $K^+$ | about 20–130 mmol/L |
| $Mg^{++}$ | about 30–40 mmol/L |
| $Cl^-$ | about 2–20 mmol/L |
| $SO_4^{2-}$ | about 80–95 mmol/L |
| Raffinose | about 20–60 mmol/L |

6. The solution of claim 5, wherein the polyethylene glycol has a molecular weight of about 4600.

7. The solution of claim 6, wherein the solution contains 10 percent by weight of polyethylene glycol.

* * * * *

UNITED STATES PATENT AND TRADEMARK OFFICE
CERTIFICATE OF CORRECTION

PATENT NO.    : 6,060,232
DATED         : May 9, 2000
INVENTOR(S)   : Von Baeyer et al.

It is certified that error appears in the above-identified patent and that said Letters Patent is hereby corrected as shown below:

Title page,
Abstract,
Line 5, delete "MgH" and insert -- $Mg^{++}$ --
Line 6, delete "aph" and insert -- a ph --

Claim 1,
Line 1, delete "coonsisting" and insert -- consisting --

Claim 5,
Line 2, inside the table, delete "20-130 mmol/L" and insert -- 70-130 mmol/L --

Signed and Sealed this

Twenty-third Day of October, 2001

Attest:

*Nicholas P. Godici*

NICHOLAS P. GODICI
*Attesting Officer*     *Acting Director of the United States Patent and Trademark Office*